US012653502B2

(12) United States Patent
Sato

(10) Patent No.: US 12,653,502 B2
(45) Date of Patent: Jun. 16, 2026

(54) ULTRASOUND TRANSDUCER, ULTRASOUND ENDOSCOPE, AND METHOD OF MANUFACTURING ULTRASOUND TRANSDUCER

(71) Applicant: OLYMPUS CORPORATION, Tokyo (JP)

(72) Inventor: Sunao Sato, Yamato (JP)

(73) Assignee: OLYMPUS CORPORATION, Tokyo (JP)

( * ) Notice: Subject to any disclaimer, the term of this patent is extended or adjusted under 35 U.S.C. 154(b) by 186 days.

(21) Appl. No.: 17/959,485

(22) Filed: Oct. 4, 2022

(65) Prior Publication Data

US 2023/0023211 A1     Jan. 26, 2023

Related U.S. Application Data

(63) Continuation of application No. PCT/JP2020/015874, filed on Apr. 8, 2020.

(51) Int. Cl.
    *A61B 8/00*        (2006.01)
    *G10K 11/02*      (2006.01)

(52) U.S. Cl.
    CPC ............ *A61B 8/4483* (2013.01); *G10K 11/02* (2013.01)

(58) Field of Classification Search
    CPC ......... A61B 8/4483; A61B 8/445; A61B 8/12; G10K 11/02; B06B 2201/55; B06B 2201/76; B06B 1/0215; B06B 1/0633
    See application file for complete search history.

(56) References Cited

U.S. PATENT DOCUMENTS

| | | | | |
|---|---|---|---|---|
| 5,735,282 A | * | 4/1998 | Hossack | .............. A61B 8/4281 |
| | | | | 600/458 |
| 2001/0041837 A1 | | 11/2001 | Takeuchi et al. | |
| 2009/0088643 A1 | | 4/2009 | Aoki et al. | |
| 2012/0302888 A1 | * | 11/2012 | Dai | .......................... A61B 8/12 |
| | | | | 29/25.35 |
| 2014/0221841 A1 | * | 8/2014 | Okuda | .................. B06B 1/0677 |
| | | | | 600/459 |
| 2017/0303893 A1 | * | 10/2017 | Sato | ........................ A61B 8/445 |
| 2021/0251604 A1 | * | 8/2021 | Sudol | ..................... B06B 1/0622 |
| 2022/0120718 A1 | * | 4/2022 | Gómez Álvarez-Arenas | .............. |
| | | | | G01N 29/245 |

FOREIGN PATENT DOCUMENTS

| | | | |
|---|---|---|---|
| JP | 2004-073631 | A | 3/2004 |
| JP | 2009-082612 | A | 4/2009 |
| JP | 4590277 | B2 | 12/2010 |
| JP | 2011-130477 | A | 6/2011 |

OTHER PUBLICATIONS

International Search Report dated Jun. 30, 2020 received in PCT/JP2020/015874.
Chinese Office Action dated Mar. 7, 2025 received in 202080099356.9.

* cited by examiner

*Primary Examiner* — Anh Tuan T Nguyen
*Assistant Examiner* — Dean N Edun
(74) *Attorney, Agent, or Firm* — Scully, Scott, Murphy & Presser, P.C.

(57) ABSTRACT

An ultrasound transducer includes: an acoustic matching layer; plural piezoelectric elements arrayed on the acoustic matching layer; and plural blocks arranged adjacent to at least one of ends of the piezoelectric elements in an elevation direction of the piezoelectric elements, each of the plural blocks including an abrasive.

19 Claims, 4 Drawing Sheets

ULTRASOUND TRANSDUCER, ULTRASOUND ENDOSCOPE, AND METHOD OF MANUFACTURING ULTRASOUND TRANSDUCER

CROSS-REFERENCE TO RELATED APPLICATION

This application is a continuation of International Application No. PCT/JP2020/015874, filed on Apr. 8, 2020, the entire contents of which are incorporated herein by reference.

BACKGROUND

1. Technical Field

The present disclosure relates to an ultrasound transducer, an ultrasound endoscope, and a method of manufacturing the ultrasound transducer.

2. Related Art

In the related art, an ultrasound endoscope includes a radial ultrasound transducer including plural piezoelectric elements arrayed in a cylindrical form (see, for example, Japanese Patent No. 4590277). Ultrasound transducers have a structure with plural piezoelectric elements arrayed by formation of plural grooves in a piezoelectric element layer that is on an acoustic matching layer by use of a dicing saw, for example. When lead zirconate titanate (PZT) used for piezoelectric elements is cut by a dicing saw, for example, the dicing saw is clogged and frictional force against the dicing blade is increased. There has thus been a problem that cracking and chipping are caused when a piezoelectric element layer continues to be cut by a dicing blade with increased frictional force.

Techniques for cutting piezoelectric element layers have been proposed to prevent these chipping and cracking upon the cutting. In one of these techniques, cutting is performed after electrically conductive resin layers are formed on the top and at the bottom of a piezoelectric element layer (see, for example, Japanese Patent Application Laid-open No. 2011-130477).

SUMMARY

In some embodiments, an ultrasound transducer includes: an acoustic matching layer; plural piezoelectric elements arrayed on the acoustic matching layer; and plural blocks arranged adjacent to at least one of ends of the piezoelectric elements in an elevation direction of the piezoelectric elements, each of the plural blocks including an abrasive.

In some embodiments, an ultrasound endoscope includes the ultrasound transducer.

In some embodiments, provided is a method of manufacturing an ultrasound transducer including an acoustic matching layer, plural piezoelectric elements arrayed on the acoustic matching layer, and plural blocks arranged adjacent to at least one of ends of the piezoelectric elements in an elevation direction of the piezoelectric elements, each of the plural blocks including an abrasive. The method includes: forming, along the elevation direction, plural grooves for the piezoelectric elements, by cutting the blocks before cutting the piezoelectric elements, by cutting the blocks after cutting the piezoelectric elements, or by cutting the blocks before and after cutting the piezoelectric elements.

The above and other features, advantages and technical and industrial significance of this disclosure will be better understood by reading the following detailed description of presently preferred embodiments of the disclosure, when considered in connection with the accompanying drawings.

DETAILED DESCRIPTION

Embodiments of an ultrasound endoscope according to the disclosure will be described hereinafter by reference to the drawings. The disclosure is not limited by these embodiments. The disclosure is generally applicable to an ultrasound endoscope including a radial ultrasound transducer but is also applicable to an ultrasound endoscope including a convex ultrasound transducer.

Any elements that are the same or corresponding to each other are assigned with the same reference sign throughout the drawings, as appropriate. It also needs to be noted that the drawings are schematic, and relations between dimensions of each element therein and proportions between the elements therein may be different from the actual ones. The drawings may also include a portion that differs in its dimensional relations or proportions between the drawings.

EMBODIMENTS

Figure 1:
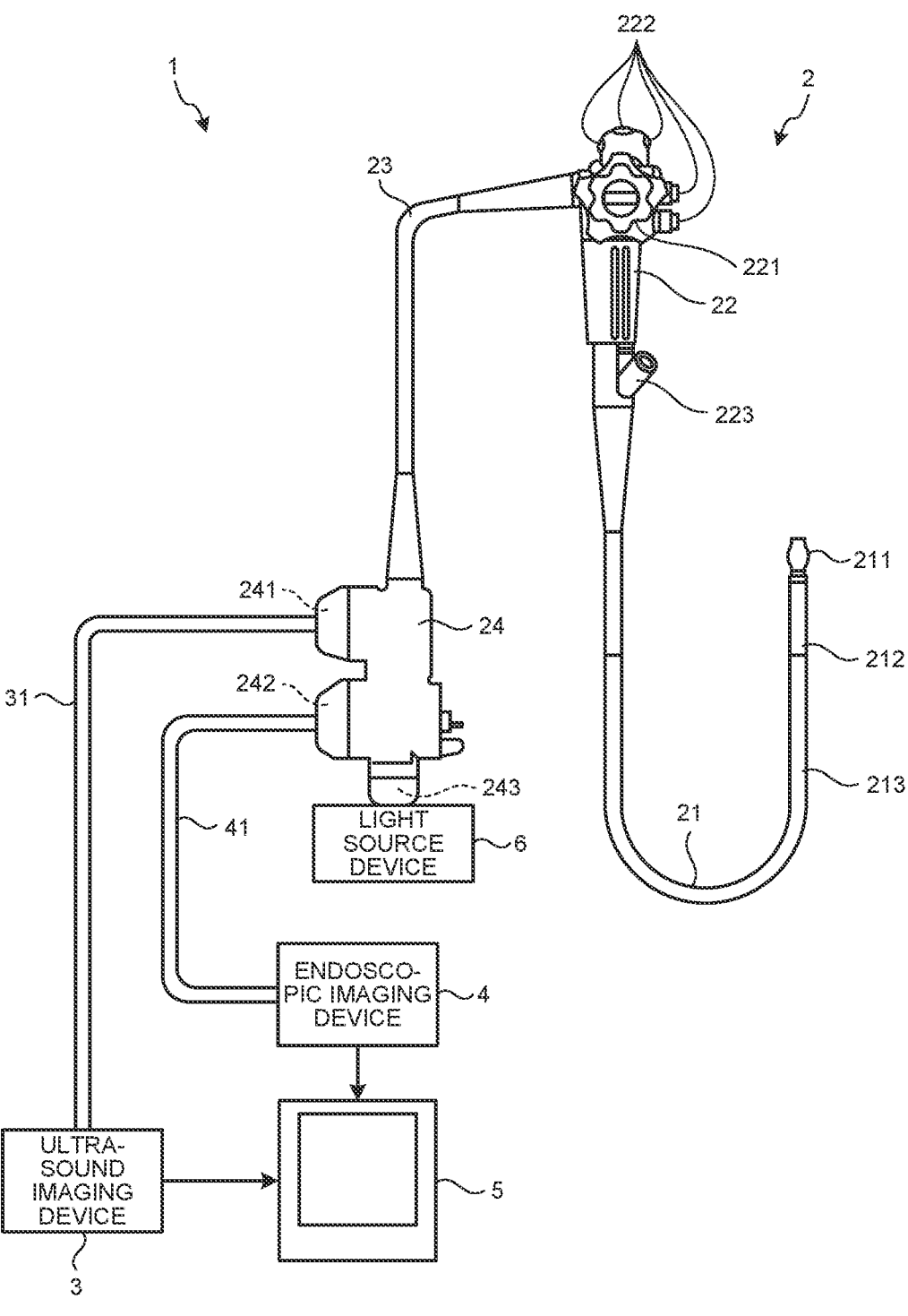
FIG. 1 is a diagram schematically illustrating an ultrasound endoscope including an ultrasound transducer according to an embodiment.

FIG. 1 is a diagram schematically illustrating an ultrasound endoscope including an ultrasound transducer according to an embodiment. An ultrasound endoscope system 1 according to the embodiment is a system for ultrasound diagnosis of the interior of a subject, such as a person, by use of an ultrasound endoscope. This ultrasound endoscope system 1 includes, as illustrated in FIG. 1, an ultrasound endoscope 2, an ultrasound imaging device 3, an endoscopic imaging device 4, a display device 5, and a light source device 6.

The ultrasound endoscope 2 is a combination of: an ultrasound probe; and an endoscopic observation unit including an imaging element and an observation optical system including a lens, for example, and has an endoscopic observation function and an ultrasound observation function. The ultrasound endoscope 2 is a radial ultrasound endoscope for ultrasound observation in a direction orthogonal to a direction in which an insertion unit is inserted.

The ultrasound endoscope 2 includes, at a distal end thereof, the ultrasound transducer that converts an electric pulse signal transmitted from the ultrasound imaging device 3 into ultrasound pulses (acoustic pulses), irradiates the subject with the ultrasound pulses, converts ultrasound echoes reflected in the subject into an electric echo signal representing the ultrasound echoes as change in voltage, and outputs the electric echo signal. A configuration of the ultrasound transducer will be described later.

The ultrasound endoscope 2 includes an illumination unit that irradiates the subject with illumination light, and an imaging unit that receives reflected light from the subject. The illumination unit includes a light guide that guides the illumination light, with which the subject is irradiated, to the distal end of the ultrasound endoscope 2 at the time of optical imaging. This light guide has: a distal end portion that reaches a distal end of the insertion unit to be inserted into the subject of the ultrasound endoscope 2; and a proximal end portion connected to the light source device 6 that generates the illumination light. The imaging unit includes an imaging optical system and an imaging element, and is capable of: being inserted into the digestive tract (esophagus, stomach, duodenum, and large intestine) or the respiratory organs (trachea and bronchi) of the subject; and imaging the digestive tract or the respiratory organs. Furthermore, the ultrasound endoscope 2 is capable of imaging organs surrounding the digestive tract and respiratory organs (pancreas, gall bladder, bile duct, pancreatic duct, lymph nodes, organs in the mediastinal space, and blood vessels, for example) by using ultrasound.

The ultrasound imaging device 3 is electrically connected to the ultrasound endoscope 2 via an ultrasound cable 31, outputs a pulse signal to the ultrasound endoscope 2 via the ultrasound cable 31, and receives an echo signal from the ultrasound endoscope 2 via the ultrasound cable 31. The ultrasound imaging device 3 generates an ultrasound image by performing predetermined processing on the echo signal.

The endoscopic imaging device 4 is electrically connected to the ultrasound endoscope 2 via a video cable and receives an image signal from the ultrasound endoscope 2 via a video cable 41. The endoscopic imaging device 4 generates an endoscopic image by performing predetermined processing on the image signal.

The display device 5 is formed by use of, for example, liquid crystal or organic electroluminescence (EL), and displays thereon, for example, an ultrasound image generated by the ultrasound imaging device 3 or an endoscopic image generated by the endoscopic imaging device 4.

The light source device 6 supplies illumination light to the ultrasound endoscope 2 via the light guide.

The ultrasound endoscope 2 includes, as illustrated in FIG. 1, an insertion unit 21, an operating unit 22, a universal cord 23, and a connector 24. A "distal end" referred to hereinafter means an end positioned in a distal end direction in which the insertion unit 21 is inserted into the subject. A "proximal end" referred to hereinafter means an end positioned in an opposite direction (toward the operating unit 22) opposite to the distal end direction in which the insertion unit 21 is inserted into the subject.

The insertion unit 21 is a tubular portion to be inserted into the subject. This insertion unit 21 includes, as illustrated in FIG. 1: an ultrasound transducer 211 positioned at the distal end of the insertion unit 21; a bendable portion 212 that is connected to a proximal end of the ultrasound transducer 211 and is bendable; and a flexible tube portion 213 that is connected to a proximal end of the bendable portion 212 and has flexibility. A configuration of a distal end portion of the insertion unit 21 will be described later.

The ultrasound transducer 211 emits ultrasound in a direction perpendicular to a longitudinal direction of the insertion unit 21. The ultrasound transducer 211 includes plural piezoelectric elements described later; and piezoelectric elements to be involved in transmission and reception are electronically changed, transmission and reception by the piezoelectric elements are delayed, and the piezoelectric elements are thereby caused to perform electronic scanning. The piezoelectric elements are caused to vibrate by input of a pulse signal, and this vibration causes the ultrasound transducer 211 to irradiate the interior of the subject with ultrasound. Furthermore, when ultrasound reflected by the subject is transmitted to the piezoelectric elements, the piezoelectric elements are caused to vibrate by the ultrasound transmitted, and the piezoelectric elements convert this vibration in to an electric signal (an echo signal). This echo signal is transmitted to the ultrasound imaging device 3 via the ultrasound cable 31, for example.

The operating unit 22 is a portion that is connected to a proximal end of the insertion unit 21 and receives various operations from a medical doctor, for example. This operating unit 22 includes, as illustrated in FIG. 1, a bending knob 221 for bending operation of the bendable portion 212, and plural operating members 222 for various operations. Furthermore, the operating unit 22 has a treatment tool insertion opening 223 formed therein. The treatment tool insertion opening 223 is for insertion of a treatment tool into a treatment tool insertion channel.

The universal cord 23 is a cable that extends from the operating unit 22, and has, arranged therein, for example: plural signal cables that transmit various signals; and an optical fiber that transmits illumination light supplied from the light source device 6.

The connector 24 is provided at a distal end of the universal cord 23. The connector 24 includes first to third connector portions 241 to 243 to which the ultrasound cable 31, the video cable 41, and the light source device 6 are respectively connected.

Figure 2:
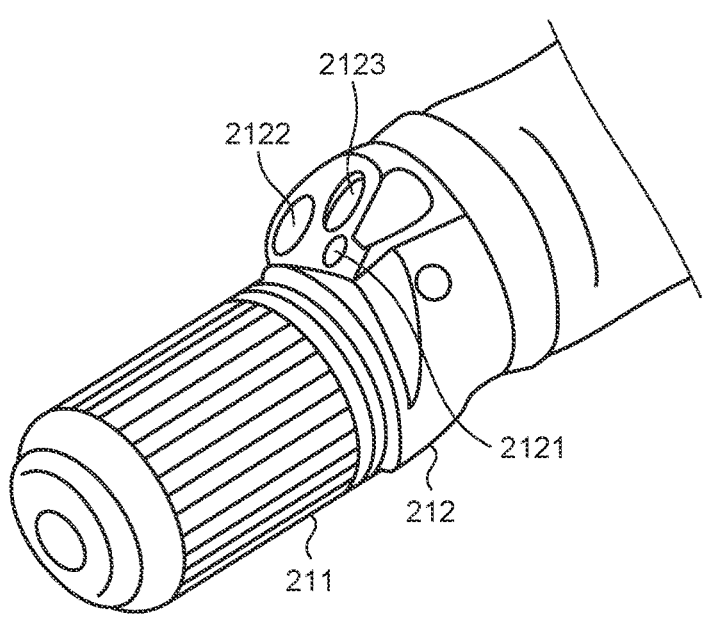
FIG. 2 is a perspective view of a distal end of an insertion unit of the ultrasound endoscope illustrated in FIG. 1.

FIG. 2 is a perspective view of a distal end portion of the insertion unit of the ultrasound endoscope illustrated in FIG. 1. As illustrated in FIG. 2, an illumination unit 2121 from which illumination light from the light source device 6 is emitted to the subject, an imaging unit 2122 including the imaging element that receives reflected light from the subject, a forceps opening 2123 also serving as a suction opening, and a gas feeding and water feeding nozzle not illustrated in the drawings are arranged in the distal end portion of the insertion unit 21.

Figure 3:
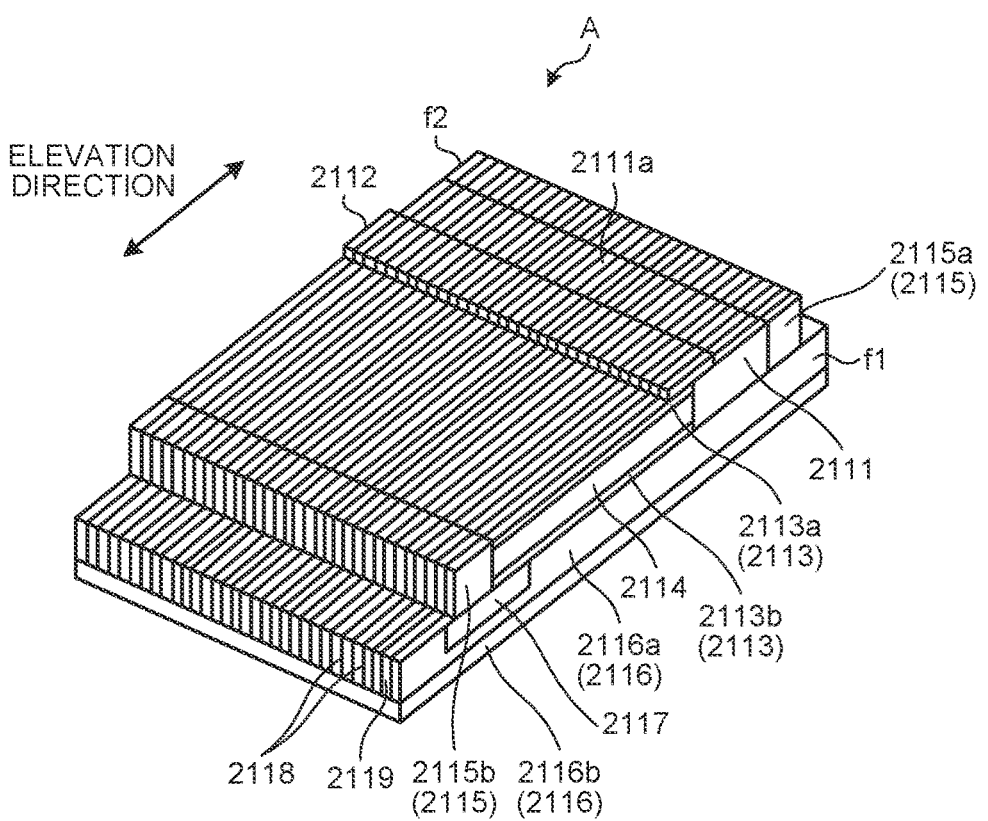
FIG. 3 is a diagram for explanation of manufacture of the ultrasound transducer according to the embodiment.
Figure 4:
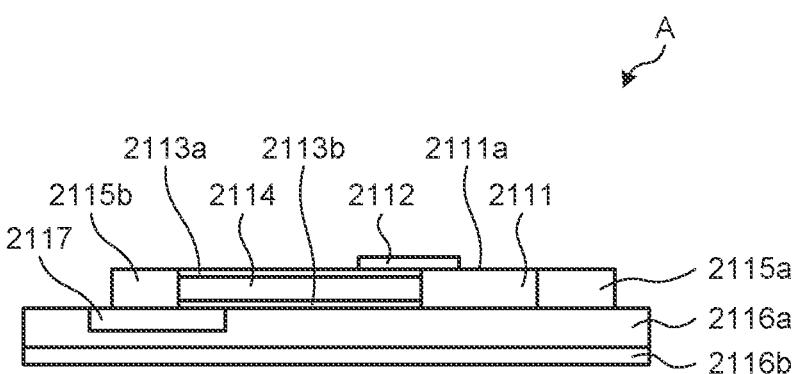
FIG. 4 is a side view of a structure in FIG. 3.

FIG. 3 is a diagram for explanation of manufacture of the ultrasound transducer according to the embodiment. A structure A illustrated in FIG. 3 includes a substrate 2111, an electrically conductive member 2112, an electrode 2113, a piezoelectric element layer 2114, a block 2115, and an acoustic matching layer 2116.

The piezoelectric element layer 2114 includes plural piezoelectric elements 2114 that are elongated and arrayed in parallel along an elevation direction (a longitudinal direction of the piezoelectric elements 2114) illustrated in FIG. 3. Each of the plural piezoelectric elements 2114 receives ultrasound. Specifically, the piezoelectric elements 2114 each convert an electric pulse signal into acoustic pulses emitted to the subject, convert ultrasound echoes reflected in the subject into an electric echo signal representing the reflected ultrasound echoes as change in voltage, and output the electric echo signal.

The substrate 2111 is arranged adjacent to one end of the piezoelectric element layer 2114 in the elevation direction. An electrode 2111a is formed on an upper surface (a surface that is opposite to a surface facing the acoustic matching layer 2116) of the substrate 2111.

An electrode 2113a is formed on an upper surface (a surface that is opposite to a surface facing the acoustic matching layer 2116) of the piezoelectric element layer 2114. An electrode 2113b is formed on a lower surface (a surface facing the acoustic matching layer 2116) of the piezoelectric element layer 2114. The electrically conductive member 2112 is arranged on top of the boundary between the substrate 2111 and the piezoelectric element layer 2114, for the purpose of electric conduction between the electrode 2111a and the electrode 2113a.

The block 2115 includes a block 2115a and a block 2115b that are arranged adjacent to ends of the piezoelectric element layer 2114 in the elevation direction. In this embodiment, the block 2115b is arranged in contact with one of the ends of the piezoelectric element layer 2114 in the elevation direction (the end on the shallower side of FIG. 3) and the block 2115a is arranged at an end of the substrate 2111 in the elevation direction (the end on the deeper side of FIG. 3).

The block 2115 is a structure including an abrasive. A structure having abrasive particles adhered and fixed to the structure may be used as the block 2115. Examples of the abrasive include diamond, zirconium oxide, alumina, silicon carbide, boron nitride, and boron carbide. In terms of hardness, for example, alumina or silicon carbide may be preferably used. Furthermore, sizes of the abrasive particles used may be about 1 μm to 30 μm.

In this embodiment, the blocks 2115a and 2115b are arranged adjacent to the two ends of the piezoelectric element layer 2114 in the elevation direction, but the block 2115 may be arranged at at least one of the ends of the piezoelectric element layer 2114 in the elevation direction. Furthermore, in this embodiment, the block 2115a is arranged adjacent to one of the ends of the piezoelectric element layer 2114 in the elevation direction, with the substrate 2111 between that end of the piezoelectric element layer 2114 and the block 2115a, but in an ultrasound transducer without the substrate 2111, the block 2115a may be arranged to be in contact with the end of the piezoelectric element layer 2114 in the elevation direction. The blocks 2115a and 2115b are preferably arranged to be in contact with the piezoelectric element layer 2114 and the substrate 2111 so that the ultrasound transducer 211 is decreased in length and size, but as long as the blocks 2115a and 2115b are arranged to be adjacent to the piezoelectric element layer 2114 and the substrate 2111, the blocks 2115a and 2115b are not necessarily in contact with the piezoelectric element layer 2114 and the substrate 2111.

The acoustic matching layer 2116 includes: a first acoustic matching layer 2116a arranged at one side of the acoustic matching layer 2116, the one side being in contact with the piezoelectric element layer 2114, for example; and a second acoustic matching layer 2116b arranged on an opposite side of the first acoustic matching layer 2116a, the opposite side being opposite to a side of the first acoustic matching layer 2116a, the side of the first acoustic matching layer 2116a facing the piezoelectric element layer 2114. The first acoustic matching layer 2116a has a cavity formed at a portion of the first acoustic matching layer 2116a, the portion contacting the boundary between the block 2115b and the piezoelectric element layer 2114, and a ground 2117 made of an electrically conductive material is provided in the cavity.

The structure A has a structure with plural transducer elements 2119 arranged on the second acoustic matching layer 2116b, with grooves 2118 between the plural transducer elements 2119. The plural transducer elements 2119 include the substrate 2111, the electrically conductive member 2112, the electrode 2113, the piezoelectric element layer 2114, the block 2115, and the first acoustic matching layer 2116a.

The structure A illustrated in FIG. 3 is manufactured by: joining the piezoelectric element layer 2114 provided with the electrode 2113, the substrate 2111 provided with the electrode 2111a, and the blocks 2115a and 2115b, to the acoustic matching layer 2116 having the ground 2117 formed therein; forming the electrically conductive member 2112; and thereafter forming the grooves 2118 by using a dicing saw, for example.

The plural grooves 2118 formed in the piezoelectric element layer 2114 are formed at regular intervals. The grooves 2118 are not formed in the second acoustic matching layer 2116b, and are formed in the first acoustic matching layer 2116a, the block 2115a, the substrate 2111 provided with the electrode 2111a, the electrically conductive member 2112, the piezoelectric element layer 2114 provided with the electrode 2113, and the block 2115b.

In a case where the grooves 2118 are formed from the deeper right side of FIG. 3, for example, the grooves 2118 are formed by the dicing saw cutting in the order, the block 2115a, the substrate 2111 provided with the electrode 2111a, the piezoelectric element layer 2114 provided with the electrode 2113, and the block 2115b. Or, in a case where the grooves 2118 are formed from the shallower left side of FIG. 3, the grooves 2118 are formed by the dicing saw cutting in the order, the block 2115b, the piezoelectric element layer 2114 provided with the electrode 2113, the substrate 2111 provided with the electrode 2111a, and the block 2115a. In this embodiment, the blocks 2115a and 2115b are cut before and after the piezoelectric element layer 2114 is cut. By cutting the blocks 2115a and 2115b, the dicing saw is able to eliminate clogging in the dicing blade. As a result, frictional force against the dicing blade is able to be reduced. Therefore, even if the grooves 2118 are formed successively by cutting the piezoelectric element layer 2114 and forming the piezoelectric elements 2114, chipping and cracking of the piezoelectric elements 2114 are able to be prevented. In this embodiment, the blocks 2115a and 2115b are cut before and after the piezoelectric element layer 2114 is cut, but in forming at least one of the grooves 2118, as long as the block 2115 is cut before the piezoelectric element layer 2114 is cut or the block 2115 is cut after the piezoelectric element layer 2114 is cut, chipping and cracking of the piezoelectric elements 2114 are able to be prevented.

Figure 5:
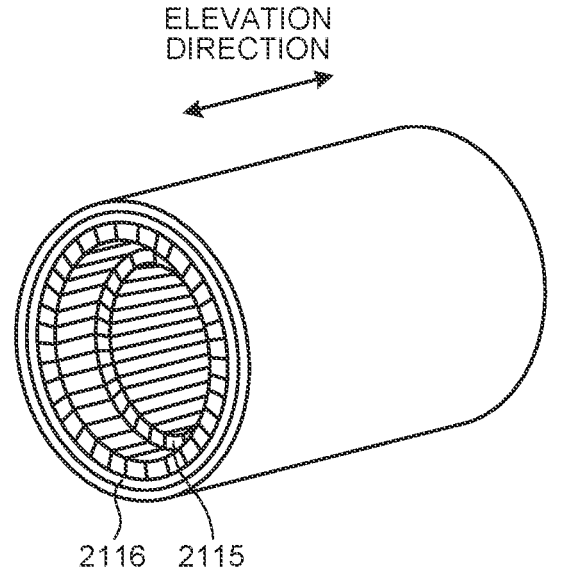
FIG. 5 is a diagram for explanation of the manufacture of the ultrasound transducer according to the embodiment.

The ultrasound transducer is able to be manufactured by: making side surfaces f1 and f2 of the structure A face each other, the side surfaces f1 and f2 being parallel to the elevation direction, to form the structure A into a cylindrical shape illustrated in FIG. 5; forming, around the cylindrically shaped structure A, an acoustic lens (not illustrated in the drawings) serving as an ultrasound transmitting and receiving unit; and connecting a cable (not illustrated in the drawings) to the electrode 2111a on the substrate 2111.

Figure 6:
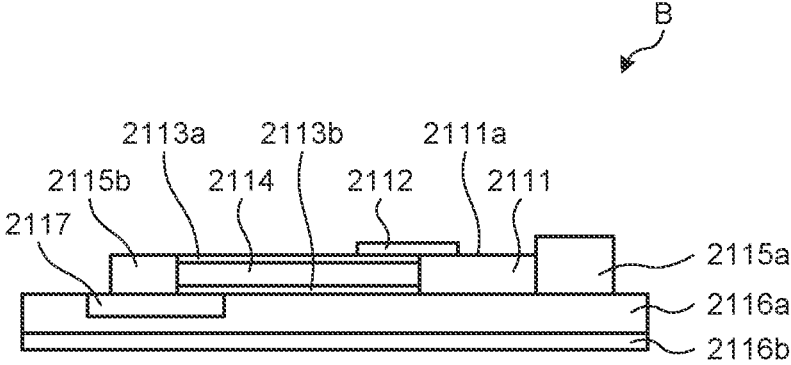
FIG. 6 is a diagram for explanation of manufacture of an ultrasound transducer according to a modified example of the embodiment.

In the above described embodiment, height of the blocks 2115a and 2115b from the acoustic matching layer 2116 is the same as height of the piezoelectric element layer 2114 from the acoustic matching layer 2116, and when the structure A is bent to be formed into the cylindrical shape, corners of adjacent ones of the piezoelectric elements 2114 come into contact with each other and chipping and cracking may thereby be caused. To prevent these chipping and cracking, the height of the block 2115 from the acoustic matching layer 2116 may be made higher than the height of the piezoelectric element layer 2114 from the acoustic matching layer 2116. FIG. 6 is a diagram for explanation of manufacture of an ultrasound transducer according to a modified example of the embodiment.

Figure 7:
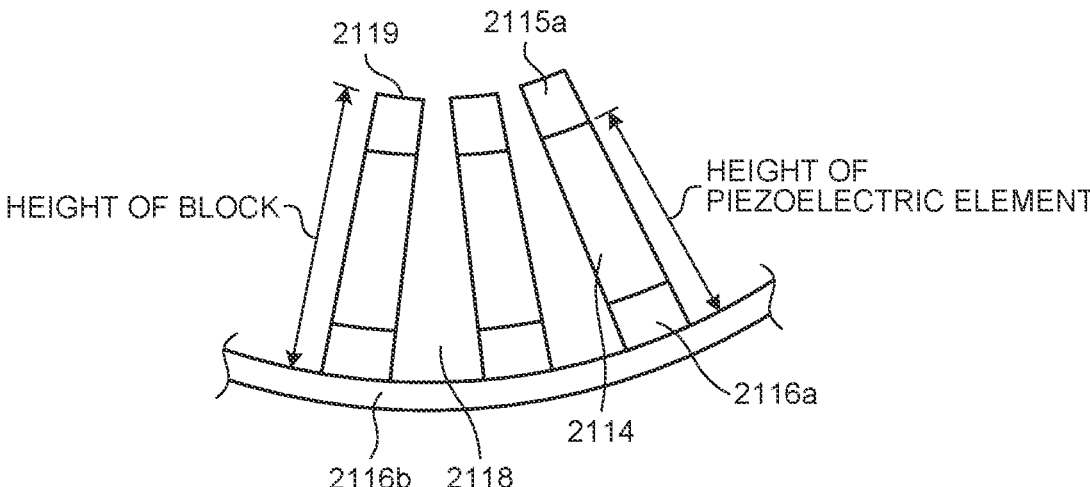
FIG. 7 is a diagram for explanation of an array of piezoelectric elements in the ultrasound transducer of FIG. 6.

In a structure B illustrated in FIG. 6, height of a block 2115*a* from an acoustic matching layer 2116 is made higher than height of a piezoelectric element layer 2114 from the acoustic matching layer 2116. FIG. 7 is a diagram for explanation of an array of piezoelectric elements in the ultrasound transducer of FIG. 6.

As illustrated in FIG. 7, in the ultrasound transducer that is bent into a cylindrical shape, distal end portions of adjacent transducer elements 2119 come close to each other near the center of the ultrasound transducer when the ultrasound transducer is bent. When the structure B is bent, any contact between distal end portions of adjacent ones of the piezoelectric elements 2114 may cause chipping, but in this modified example, because the height of the block 2115*a* has been made higher than the height of the piezoelectric element layer 2114, pieces of the block 2115*a* contact each other before the adjacent ones of the piezoelectric elements 2114 contact each other, and the adjacent ones of the piezoelectric elements 2114 are thus able to be prevented from contacting each other. The height of the block 2115*a* is a height at which adjacent pieces of the block 2115*a* do not interfere with each other when the structure B is bent into the cylindrical shape. In this modified example, only the block 2115*a* is made higher than the piezoelectric element layer 2114, but the block 2115*b* may also be made higher than the piezoelectric element layer 2114. Or, the height of the block 2115*b* may be made higher than the height of the piezoelectric element layer 2114 and the height of the block 2115*a* may be made the same as the height of the piezoelectric element layer 2114.

The disclosure enables provision of an ultrasound transducer enabling chipping and cracking to be prevented when a piezoelectric element layer is cut and having excellent performance.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound transducer, comprising:
   an acoustic matching layer;
   a plurality of piezoelectric elements provided on the acoustic matching layer;
   a plurality of blocks, each provided at at least one end of a corresponding piezoelectric element of the plurality of piezoelectric elements in an elevation direction of the plurality of piezoelectric elements, each of the plurality of blocks being provided on the acoustic matching layer; and
   a substrate arranged between each block and the corresponding piezoelectric element in the elevation direction;
   wherein the acoustic matching layer is configured to have an arc-shape with the plurality of piezoelectric elements arranged on an inside of the arc-shape; and
   during the acoustic matching layer being bent into the arc-shape, a block of the plurality of blocks and an adjacent block of the plurality of blocks contact to prevent corresponding adjacent piezoelectric elements of the plurality of piezoelectric elements from contacting.

2. The ultrasound transducer according to claim 1, wherein the plurality of blocks each comprises an abrasive, the abrasive is selected from a group consisting of alumina, silicon carbide, and a mixture of alumina and silicon carbide.

3. The ultrasound transducer according to claim 2, wherein the abrasive having a particle size ranging from 1 μm to 30 μm.

4. An ultrasound endoscope comprising the ultrasound transducer according to claim 1.

5. The ultrasound transducer according to claim 1, wherein the block of the plurality of blocks comprises a first block of a first plurality of blocks, and the ultrasound transducer further comprising a second plurality of blocks that are each in direct contact with each corresponding piezoelectric element of the plurality of piezoelectric elements.

6. The ultrasound transducer according to claim 1, wherein the plurality of blocks are each provided distally relative to each corresponding piezoelectric element of the plurality of piezoelectric elements.

7. The ultrasound transducer according to claim 1, wherein the plurality of blocks comprise a plurality of first block portions and a plurality of second block portions,
   each of the plurality of first block portions is provided distally relative to each of the plurality of piezoelectric elements, and
   each of the plurality of second block portions is provided proximally relative to each of the plurality of piezoelectric elements.

8. The ultrasound transducer according to claim 7, further comprising an electrode provided between the each of the plurality of first block portions and each of the plurality of second block portions for each of the plurality of piezoelectric elements.

9. The ultrasound transducer according to claim 7, wherein each of the plurality of second block portions is partially provided on a corresponding one of the plurality of piezoelectric elements.

10. The ultrasound transducer according to claim 9, wherein each of the plurality of second block portions is partially provided on an end surface of each of the plurality of piezoelectric elements.

11. The ultrasound transducer according to claim 7, wherein each of the plurality of second block portions is directly provided on an end surface of each of the plurality of piezoelectric elements, the end surface extending in the direction protruding from the acoustic matching layer.

12. The ultrasound transducer according to claim 1, further comprising a groove provided between adjacent piezoelectric elements of the plurality of piezoelectric elements.

13. The ultrasound transducer according to claim 12, wherein the groove is also provided between adjacent blocks provided at the at least one end of adjacent piezoelectric elements of each of the plurality of piezoelectric elements.

14. The ultrasound transducer according to claim 1, wherein in the elevation direction, a first length of the acoustic matching layer is larger than a second length of the plurality of piezoelectric elements.

15. The ultrasound transducer according to claim 1, wherein the elevation direction extends along a longitudinal direction of the plurality of piezoelectric elements.

16. The ultrasound transducer according to claim 1, wherein the plurality of blocks are each in contact with a side surface of the substrate.

17. The ultrasound transducer according to claim 1, wherein the substrate is electrically connected to the plurality of piezoelectric elements by electrodes.

18. The ultrasound transducer according to claim 1, wherein each block of the plurality of blocks has a greater height from the acoustic matching layer than at least one of (i) a height of the corresponding piezoelectric element from the acoustic matching layer or (ii) a height of the substrate from the acoustic matching layer.

19. An ultrasound transducer, comprising:

an acoustic matching layer;

a plurality of piezoelectric elements provided on the acoustic matching layer; and a block provided at at least one end of each of the plurality of piezoelectric elements in an elevation direction of the plurality of piezoelectric elements;

wherein the acoustic matching layer is configured to have an arc-shape with the plurality of piezoelectric elements arranged on an inside of the arc-shape; and during the acoustic matching layer being bent into the arc-shape, the block and an adjacent block contact to prevent corresponding adjacent piezoelectric elements of the plurality of piezoelectric elements from contacting.

\* \* \* \* \*